United States Patent [19]

Banba

[11] 4,356,259
[45] Oct. 26, 1982

[54] PRESERVING SPERM OF DOMESTIC ANIMALS

[76] Inventor: Kimio Banba, No. 1000, Orito, Shimizu-shi, Shizuoka-ken, Japan

[21] Appl. No.: 178,480

[22] Filed: Aug. 15, 1980

[30] Foreign Application Priority Data

Aug. 27, 1979 [JP] Japan .................................. 54-108123

[51] Int. Cl.³ .............................................. A01N 1/02
[52] U.S. Cl. ...................................................... 435/2
[58] Field of Search ............................................ 435/2

[56] References Cited
U.S. PATENT DOCUMENTS 3,418,209 12/1968 Ushakoff .................................. 435/2
3,846,236 11/1974 Updike ..................................... 435/2
3,953,329 4/1976 Updike ..................................... 435/2

*Primary Examiner*—Sam Rosen
*Attorney, Agent, or Firm*—William A. Drucker

[57] ABSTRACT

In a method of preserving sperm of domestic animals, especially for the purposes of artificial insemination, a quantity of the sperm, diluted if necessary with a diluting solution, is maintained in communication, through a dialytic membrane, with a quantity of Ringer's solution containing albumin or activated carbon, the whole being maintained at a constant temperature preferably of about 15° C. An antibiotic may be added to the sperm to prevent bacterial growth.

8 Claims, 2 Drawing Figures

PRESERVING SPERM OF DOMESTIC ANIMALS

BACKGROUND OF THE INVENTION

The present invention relates to a method of preserving sperm to be used for the artificial insemination of domestic animals, and especially for the artificial insemination of swine.

THE PRIOR ART

Sperms of domestic animals have heretofore been preserved at temperatures below the freezing point. For example, the freeze-preservation method has been widely employed for preserving the sperm of cattle. However, no attempt has been successful for preserving the sperm of swine because of the following reasons, namely, the insemination of swine requires sperm in amounts larger than those of other domestic animals, and there is so far available no suitable substance for protecting the sperm from the freezing temperatures.

Therefore, there has been proposed a method of preserving the sperm in a liquid state by adding a diluting solution to the sperm. This method is effective when the sperm is to be preserved for only short periods of time. When the sperm is to be preserved for 7 to 10 days, however, the above method is not capable of maintaining the spermatic activity which is necessary for accomplishing the artificial insemination. With the above-mentioned liquid preservation method, furthermore, an increased number of spermatozoa turn out to be defective in the acroworm (head cap).

Therefore, it has been attempted to preserve the sperm at a temperature of as low as several degrees centigrade to extend the time over which the sperm can be effectively preserved. According to this method, however, the sperm collected from the animal must be cooled from a temperature close to the body temperature (about 37° C.) of the animal to the cooling temperature at such a low rate as 1° to 2° C. per hour. Therefore, the lower the preservation temperature, the longer the cooling time required, while necessitating a specially designed cooling apparatus.

OBJECT OF THE INVENTION

The object of the present invention is to provide a method of preserving the sperm which is free from the defects inherent in the above-mentioned conventional methods, which helps maintain the spermatic activity which is necessary for the artificial insemination even when the sperm is preserved for extended periods of time, which prevents the spermatozoa from becoming defective during the preservation, and which does not require any complicated cooling operation.

SUMMARY OF THE INVENTION

The present invention involves a method of preserving the sperm of a domestic animal by contacting through a dialytic membrane said sperm with a Ringer's solution containing albumin or activated carbon.

BRIEF DESCRIPTION OF THE DRAWINGS

The drawings illustrate a preservation vessel used for putting the method of the present invention into practice, FIG. 1 being a cross-sectional view, and
FIG. 2 being a plan view.

DESCRIPTION OF THE PREFERRED EMBODIMENT

Figure 1:
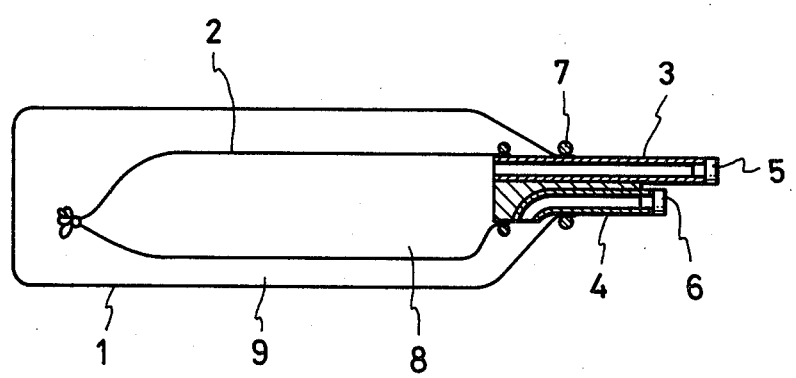

The method of the present invention is put into practice by using a vessel shown schematically in FIG. 1. The vessel 1 contains a dialytic tube 2 which has an injection port 3. An injection port 4 is also formed in the space between the dialytic tube 2 and the vessel 1. The injection ports 3 and 4 are secured by a ring 7, and are hermetically closed by plugs 5 and 6, respectively.

The sperm which is collected or the sperm which is diluted with a diluting solution is injected into the dialytic tube 2, and the injection port is hermetically sealed by the plug 5. A Ringer's solution 9 containing albumin or activated carbon is injected into the space between the dialytic tube 2 and the vessel 1. The vessel 1 containing the sperm 8 and the Ringer's solution is preserved in a refrigerator maintained at a constant temperature (which is desirably set at about 15° C.).

The method of the present invention is effective for preserving the sperm presumably because of the reasons mentioned below.

At a preservation temperature of about 15° C., the activity of the sperm is halted but the metabolism continues. Consequently, nutrients such as carbohydrates are consumed, and substances such as organic wastes which are harmful to the survival of the spermatozoa are formed.

Proteins such as albumins or the activated carbon works to adsorb harmful substances such as organic wastes and, hence, presumably remove harmful substances, formed in the sperm, through the dialytic membrane. The albumin can be selected from glair albumin, serum albumin, and the like. The activated carbon should be washed with hot water and should be relieved of harmful substances such as chlorine and the like.

Although it may vary depending upon the shape of the preservation vessel, the albumin or the activated carbon exhibits sufficient effects when it is used in the amount of a dialytic solution (about 0.5 to about 1.0% for the albumin, and about 0.25 to about 0.5 NT% for the activated carbon). The Ringer's solution is saline water containing about 0.9% of sodium chloride, and works to dissolve or disperse the albumin or the activated carbon as well as to adjust the ion concentrations and pH values inside and outside the dialytic membrane. In the specification of the present application, however, saline waters to which is added a reflux for artificial kidney use, such as a KRB solution (KreboRinger bicarbonate solution), or a KRP solution (Krebo-Ringer phosphate solution) in addition to the sodium chloride, will also be referred to as the Ringer's solution. An anti-biotic substance such as streptomycin or sulpenicillin may be added to the sperm which is to be preserved so that the spermatozoa are prevented from being killed by the propagation of bacteria.

Figure 2:
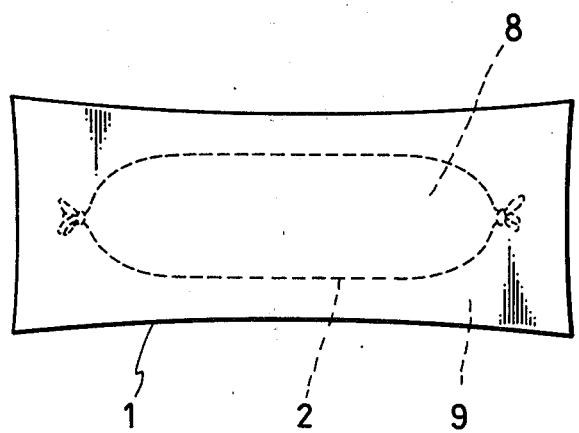

The dialytic membrane is a film having fine pores of a size which permits the organic wastes formed in the sperm to pass through but does not permit the spermatozoa or the albumin or the activated carbon to pass through. The dialytic membrane can be prepared by utilizing a commercially available dialytic membrane for artificial kidneys made of a cellulose film or a plastic film, or by utilizing a porous film. In the embodiment shown in FIG. 1, the sperm 8 is contained on the inner side of the dialytic tube 2, and the Ringer's solution 9 is contained on the outer side of the dialytic tube 2. As illustrated in FIG. 2, furthermore, the dialytic tube 2 may be hermetically sealed and immersed in the dialytic solution without being fitted with the plug. In other words, the vessel may be of any shape provided the sperm and the Ringer's solution are permitted to come into contact with each other via the dialytic membrane.

In preserving the sperm, good results can be obtained when the dialytic tube 2 is maintained horizontally, rather than vertically supported. This is presumably due to the fact that organic wastes can be easily removed when the spermatozoa precipitated by the force of gravity are dispersed over wide areas on the surface of the dialytic membrane.

EXAMPLE 1

The sperm of a swine contained in the vessel 1 shown in FIG. 2 was preserved for 7 days in a refrigerator in which the temperature was maintained at 15° C., to measure the activity of the spermatozoa and the ratio of spermatozoa having a normal head cap. The results were as shown in Table 2. The sperm preserved was also introduced into the dialytic tube 2 in its own form and was dialyzed with Ringer's solutions of compositions as shown in Table 1.

TABLE 1

| No. | Sperm | Composition of Ringer's solution |
|---|---|---|
| 1 | 5ml of sperm in its own form | 20ml of KRB solution containing 0% of adsorbing agent, and 20% of glucose solution at a concentration of 5.05% |
| 2 | same as above | 20ml of KRB solution containing 0.125% of activated carbon and 25% of glucose solution at a concentration of 5.05% |
| 3 | same as above | 20ml of KRB solution containing 0.25% of activated carbon and 25% of glucose solution at a concentration of 5.05% |
| 4 | same as above | 20ml of KRB solution containing 0.5% of activated carbon and 25% of glucose solution at a concentration of 5.05% |
| 5 | same as above | 20ml of KRB solution containing 1.0% of activated carbon and 25% of glucose solution at a concentration of 5.05% |
| 6 | same as above | 20ml of KRB solution containing 2.0% of activated carbon and 25% of glucose solution at a concentration of 5.05% |

TABLE 2

| Specimen No. | Spermatic activity (%) | | Ratio of spermatozoa having normal head cap | | |
|---|---|---|---|---|---|
| | Before preservation | After preservation for 7 days | Before preservation | After preservation for 7 days | |
| 1 | 95 +++ | 58.4 ± 11.9 | 89 +++ | 47.0 ± 13.1 | KG31 + activated carbon (0%) |
| 2 | 95 +++ | 63.7 ± 10.8 | 89 +++ | 55.6 ± 12.4 | KG31 + activated carbon (0.125%) |
| 3 | 95 +++ | 69.6 ± 6.9 | 89 +++ | 62.5 ± 10.3 | KG31 + activated carbon (0.25%) |
| 4 | 95 +++ | 67.5 ± 8.7 | 89 +++ | 57.6 ± 10.2 | KG31 + activated carbon (0.5%) |
| 5 | 95 +++ | 61.8 ± 15.6 | 89 +++ | 56.0 ± 12.4 | KG31 + activated carbon (1.0%) |
| 6 | 95 +++ | 50.3 ± 18.5 | 89 +++ | 49.8 ± 12.9 | KG31 + activated carbon (2.0%) |

The collected sperm was introduced in its own form into the dialytic tube 2, inserted into the vessel 1 filled with the Ringer's solution, and after the vessel was sealed, the sperm was cooled to about 15° C. over a period of 3 to 4 hours to preserve it in a refrigerator. The thus preserved sperm was then centrifugally precipitated, and the spermatozoa were allowed to float in the KRP solution to which a glucose and a catalase had been added, to culture them at 37° C. for 1 hour. The spermatic activity was then examined. The spermatic activity was indicated by percentage (+++%) relying upon the number of actively moving spermatozoa in the sight of a microscope with the total number of spermatozoa in the sight being 100. The ratio of spermatozoa having a normal head cap was examined relying upon the samples of Dott and Foster dyed with Eosine and Nigrosine as viewed through a microscope having a magnification of 600 times. Those which were not apical ridge-deformed were regarded to be normal, and other spermatozoa were regarded as defective. The ratio of normal spermatozoa was indicated by a percentage. The Ringer's solution, to which are added, as antibiotic substances, the streptomycin in an amount of 1 mg/ml and sulpenicillin in an amount of 1 mg/ml, added to the sperm and to the dialytic solution, is usually called a KRB solution, and has the following composition:

| | | | |
|---|---|---|---|
| Sodium chloride | 0.9% solution | 100 | parts by volume |
| potassium chloride | 1.15% solution | 4 | parts by volume |
| calcium chloride | 1.22% solution | 3 | parts by volume |
| potassium dihydrogenphosphate | 2.11% solution | 1 | part by volume |
| heptahydrate of magnesium sulfate | 3.22% solution | 1 | part by volume |
| sodium bicarbonate saturated with carbon dioxide gas | 1.30% solution | 21 | parts by volume |

According to the method of the present invention as mentioned above, the spermatic activity necessary for the artificial insemination can be maintained even when the sperm is preserved for as long as 7 to 10 days, permitting the spermotozoa to become less susceptible to damage during preservation. Furthermore, since the sperm can be desirably preserved at a temperature of 15° C., which is close to room temperature, the collected sperm can be cooled to the preservation temperature simply by leaving it to cool at room temperature for 3 to 4 hours. Consequently, the method of the present invention does not require a cumbersome cooling operation which is needed for the method of low-temperature preservation.

I claim:

1. A method of preserving sperm of domestic animals comprising the steps of:

(i) encapsulating a quantity of sperm in a dialytic tube;

(ii) placing said dialytic tube in a vessel filled with Ringer's solution containing an absorbent selected from the group consisting of
  albumin and
  activated carbon
whereby a protective buffer layer of said solution surrounds said dialytic tube, and (iii) maintaining said dialytic tube and said vessel and their contents at a temperature of about 15° C.

2. The method claimed in claim 1, wherein said sperm is diluted prior to encapsulating in said dialytic tube.

3. The method claimed in claim 1 wherein the albumin is selected from the group consisting of glair albumin and serum albumin.

4. The method claimed in claim 1 comprising the step of treating the activated carbon to remove chlorine, prior to placing it in communication with the sperm.

5. The method claimed in claim 4, wherein the activated carbon is preliminarily washed with hot water.

6. The method claimed in claim 1 wherein the albumin is in a dialytic solution of 0.5% to 1.0% w/v.

7. The method claimed in claim 1 wherein the activated carbon is in a dialytic solution of 0.25% to 0.5 w/v.

8. The method claimed in claim 1 including the step of adding an anti-biotic to the sperm.

* * * * *